United States Patent [19]

Lattin

[11] 4,456,012

[45] Jun. 26, 1984

[54] IONTOPHORETIC AND ELECTRICAL TISSUE STIMULATION DEVICE

[75] Inventor: Gary A. Lattin, Forest Lake, Minn.

[73] Assignee: Medtronic, Inc., Minn.

[21] Appl. No.: 351,104

[22] Filed: Feb. 22, 1982

[51] Int. Cl.³ ............................................... A61N 1/36
[52] U.S. Cl. ................................................ 128/420 R
[58] Field of Search ............................... 128/421–423, 128/420 R; 604/20

[56] References Cited

U.S. PATENT DOCUMENTS

| | | | |
|---|---|---|---|
| 3,294,092 | 12/1966 | Landauer | 128/420 R |
| 3,646,940 | 3/1972 | Timm et al. | 128/421 |
| 3,735,756 | 5/1973 | Richards et al. | 128/421 |
| 3,851,651 | 12/1974 | Icenbice, Jr. | 128/422 |
| 3,885,573 | 5/1975 | Hara | 128/420 R |
| 3,888,261 | 6/1975 | Maurer | 128/421 |
| 3,991,755 | 11/1976 | Vernon et al. | |
| 4,141,359 | 2/1979 | Jacobsen et al. | 604/20 |
| 4,240,437 | 12/1980 | Church | 128/420 R |
| 4,301,794 | 11/1981 | Tapper | 604/20 |
| 4,340,047 | 7/1982 | Tapper et al. | 604/20 |
| 4,383,529 | 5/1983 | Webster | 604/20 |

OTHER PUBLICATIONS

Joseph Kahn, Ms, PT Article of 1981 entitled, "Electrotherapeutic Approach to Postoperative Pain Following Total Hip Replacement: A Case Study".
Medco Products Co., Inc. advertisements/specification materials.

Primary Examiner—William E. Kamm
Assistant Examiner—Mitchell J. Shein
Attorney, Agent, or Firm—Merchant, Gould, Smith, Edell, Welter & Schmidt

[57] ABSTRACT

An electrotherapeutic device for selectively providing iontophoretic or biphasic stimulation to electrodes for introducing iontophoretic substances and for delivering biphasic current to body tissue, comprising timing circuits (120, 270, 280) for providing preselected stimulation intervals, and circuits (10, 30, 50) for providing iontophoretic and biphasic stimulation (151, 152) to the electrodes in response to the timing circuits and a user actuated input (92). The timing circuits may provide alternating intervals of biphasic and iontophoretic stimulation and optionally include a user-actuated one-shot timer (120) for interrupting biphasic stimulation and providing iontophoretic stimulation for a predetermined interval.

21 Claims, 5 Drawing Figures

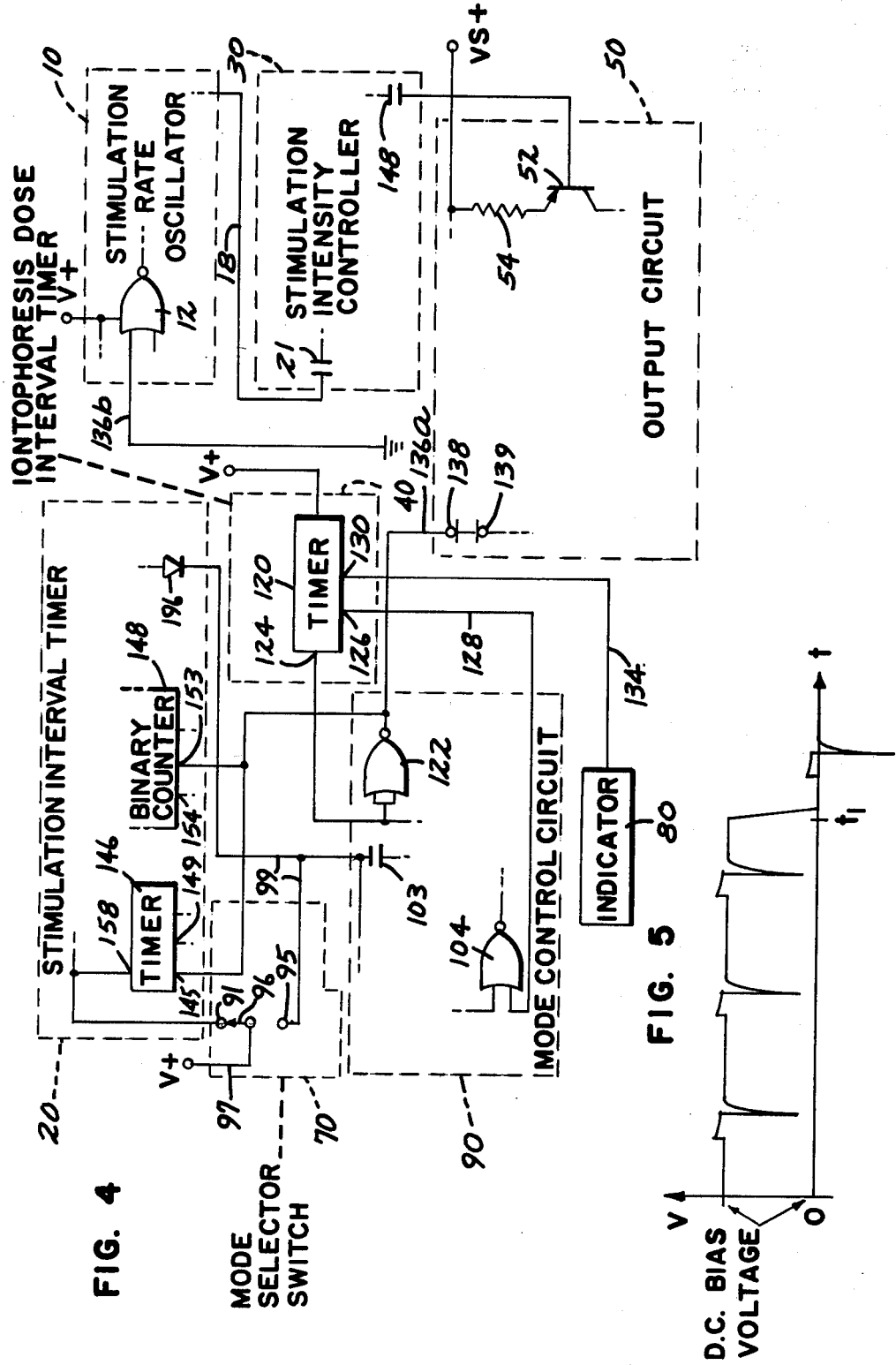

IONTOPHORETIC AND ELECTRICAL TISSUE STIMULATION DEVICE

TECHNICAL FIELD OF THE INVENTION

This invention relates generally to the field of electrotherapeutic medicine, and more particularly concerns a new device which is capable of selectively delivering iontophoretic stimulation for a predetermined duration, either automatically at predetermined intervals or manually controlled, and which is alternatively capable of delivering biphasic electrical tissue stimulation either alone or in combination with iontophoretic stimulation.

BACKGROUND OF THE INVENTION

Iontophoresis is a method for introducing ionic substances into body tissues which has proven to be very useful in numerous medical applications. The method most often utilizes direct electrical current to drive ionized substances such as chemicals or drugs placed on the skin through the intact skin or other body surface to the interior of the body. Iontophoretic systems generally comprise an iontophoretic current generator and a pair of electrodes with the ionic substance to be introduced into the body tissue contained between the appropriate polarity electrode and the body. The current generator may take any number of different forms but generally is a hand-held or table-supported instrument which is connected to the electrodes by means of leads. Because the ionic substances generally available for use with iontophoretic systems are fluid solutions or gels, electrode systems must provide seals and means for holding the electrodes securely in place. Therefore, their placement to and transfer from or on the patient's body is a task requiring relatively high skill levels.

Like iontophoresis, electrical tissue stimulation, also known as nerve stimulation, has also been proven to be useful and effective in many medical applications. One of the most common usages of electrical tissue stimulation is for the relief of chronic and acute pain. For such stimulation, both DC and AC (biphasic) currents can be used. However, biphasic stimulation is considered by those knowledgeable in the art as safer and more effective. Other applications for electrical tissue stimulation include muscle exercising, bladder stimulation and bone stimulation.

Electrical tissue stimulation may be delivered to the affected tissue transcutaneously, or it may be applied directly to subcutaneous tissue through implanted electrodes. Transcutaneous stimulators are generally carried or worn by the patient and are connected through leads to electrodes secured to the patient's body. Implantable or subcutaneous stimulators usually comprise implantable electrodes having a receiver connected thereto and a stimulation transmitter which transmits electromagnetic stimulation energy through the skin to the receiver where the energy is demodulated and delivered to the implanted electrodes. Other subcutaneous nerve stimulators provide for the implantation of the entire device, with control provided by an electromagnetic link.

Conventionally, iontophoretic and biphasic stimulation devices are used independently of each other, i.e. the corresponding stimulation methods have not been routinely or systemically integrated in treatment regimen. However, medical research indicates significant benefits where the two methods are cooperatively combined. One promising area for the integrated use of iontophoretic and biphasic tissue stimulation is for the relief or control of pain. For one example of the integration of these methods for control of pain in the field of physical therapy see Joseph Kahn, MS, PT, *Electrotherapeutic Approach to Postoperative Pain Following Total Hip Replacement: A Case Study*, The Journal of Orthopedic and Sports Physical Therapy, Spring, 1981. There are many other possible applications for the combined or integrated use of iontophoresis and electrical tissue stimulation. One possible use is in the area of sports medicine, where the integration of electrical tissue stimulation and iontophoresis could be particularly useful in dealing with joint pain and muscle rehabilitation.

Heretofore, there has not been provided a device integrating iontophoresis, electrical tissue stimulation and operating mode timing control capability in a single common-lead-and-electrode device. Therefore, in the case where the needs of the patient require or suggest iontophoretic treatment periodically interchanged with electrical tissue stimulation, the iontophoretic device must be exchanged with a tissue stimulation device, normally requiring the exchange of electrodes also. Obviously, due to the precision and care with which the iontophoresis electrodes must be attached and reattached, and the need for initial adjustments of each device, the procedure is time consuming and relatively difficult. Also, the procedure forecloses the relatively rapid alternation or interchange between the two stimuli. Furthermore, stimulus mode timing (i.e. timing of mode repetition period and duration) is complicated by the necessity of user or staff intervention.

SUMMARY OF THE INVENTION

In response to the above mentioned needs, the present invention provides an electrotherapeutic device for selectively providing either electrical tissue stimulation, for example bisphasic, or timed intervals of iontophoretic current for the introduction of ionic substances into body tissue interspersed with electrical tissue stimulation. Preferably, the device includes circuits for generating biphasic electrical tissue stimulation and iontophoretic current, with the circuits connected to deliver either stimulation to body tissue through a common set of leads and electrodes. A control circuit permits the user to manually select either mode of stimulation and additionally provides for automatic control of stimulation mode with adjustable timing means. The control circuit includes means for selecting a plurality of different intervals between iontophoretic doses, and means for timing a prescribed dose interval during which iontophoretic current is produced. The device further includes an indicator for indicating when an iontophoretic dose is being delivered.

According to another aspect of the invention, there is provided means for simultaneously producing iontophoretic current and biphasic tissue stimulation for delivery to a single pair of electrodes.

BRIEF DESCRIPTION OF THE DRAWINGS

FIG. 4 is a partial detailed schematic diagram showing a modification to the preferred embodiment of FIG. 2; and FIG. 5 is a graphic illustration of an example waveform produced by the alternative embodiment shown in FIG. 4.

DETAILED DESCRIPTION OF THE PREFERRED EMBODIMENT

Figure 1:
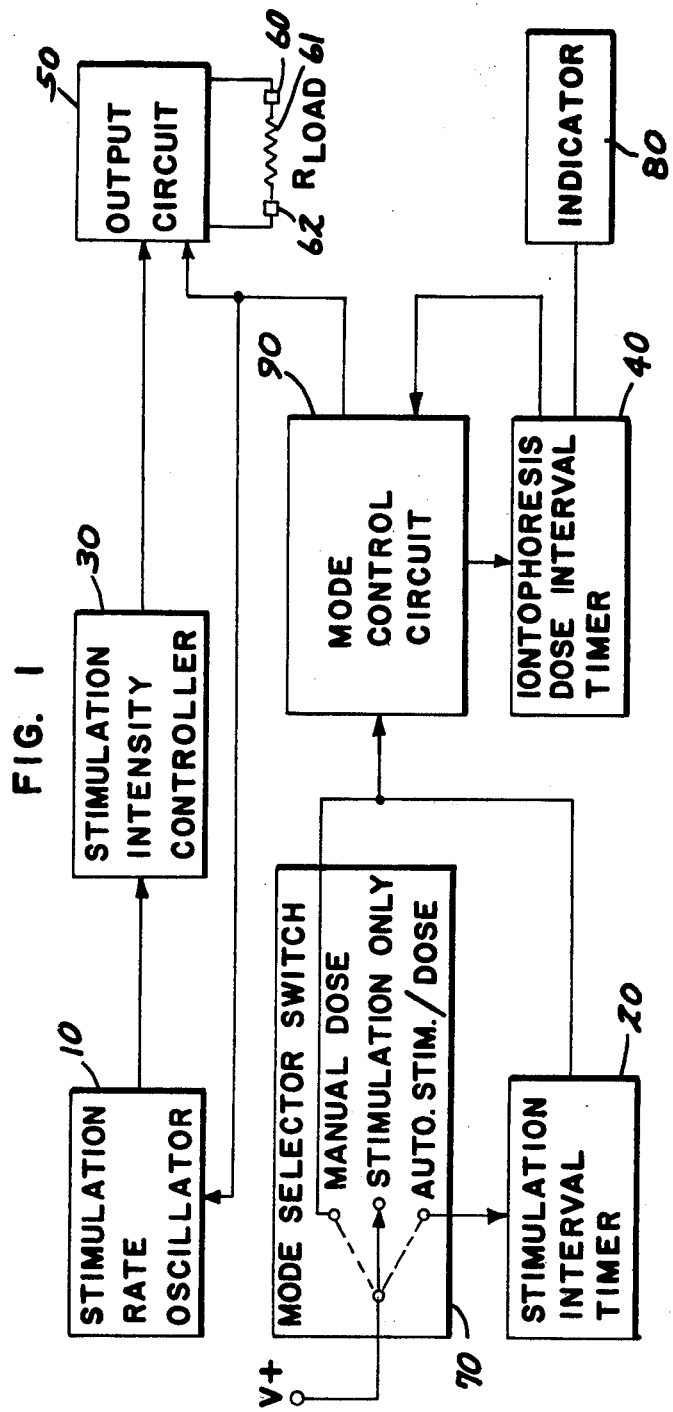
FIG. 1 is a block diagram of an iontophoretic electrical tissue stimulation device according to the preferred embodiment of the present invention.

Referring to FIG. 1 there is illustrated in block diagram form the preferred embodiment of the present invention. Stimulation rate oscillator 10, stimulation intensity controller 30 and output circuit 50 generally represent that portion of the present invention for producing biphasic electrical tissue stimulation and iontophoretic stimulation. Mode selector switch 70, mode control circuit 90, stimulation interval timer 20, iontophoresis dose interval timer 40 and indicator 80 generally represent that portion of the present invention providing mode timing control. A brief description of the operation of the present invention will now be given with respect to FIG. 1, with a more detailed description of the corresponding circuits and their operation given below with respect to FIG. 2.

Figure 3:
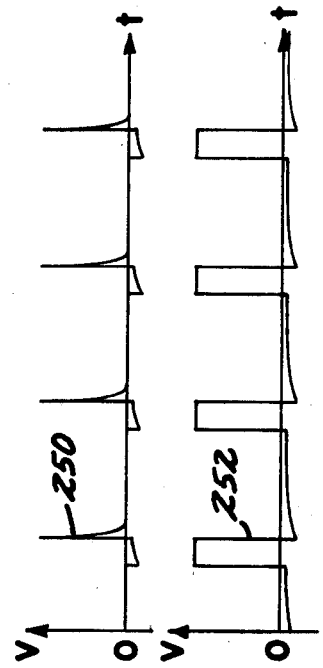
FIG. 3 is a graphic illustration of example biphasic stimulation waveforms.

The invention may operate in any one of three possible modes of operation; manual dose, stimulation only and auto stimulation/dose. The stimulation only mode, which causes biphasic electrical tissue stimulation to be produced for delivery to electrodes 60 and 62, is selected using mode selector switch 70. In this mode of operation, stimulation rate oscillator 10, stimulation intensity controller 30 and output circuit 50 cooperate to produce electrical tissue stimulation (biphasic in the preferred embodiment). Stimulation rate oscillator 10 controls the rate or frequency of the bisphasic stimulation waveform. Stimulation intensity controller 30, which is synchronized through its input from oscillator 10, controls the intensity of biphasic pulses produced by circuit 50 by modulating the duty cycle of pulses received from oscillator 10. Controller 30 includes an adjustable input for control thereof. Output circuit 50 is responsive to the frequency and duty cycle of signals received from controller 30 for producing biphasic stimulation for delivery to electrodes 60 and 62. Typical biphasic waveforms 250 and 252 are shown in FIG. 3.

In the manual dose mode, the initiation of an iontophoretic dose may be accomplished, again through mode selector switch 70. In this mode control circuit 90 is activated through its input from switch 70 in order to disable oscillator 10 and enable output circuit 50 to produce an iontophoretic DC current for delivery to electrodes 60 and 62. The duration of the iontophoretic dose interval is controlled via iontophoresis dose interval timer 40, which resets mode control circuit 90 at the end of the selected interval through its output connection thereto. Indicator 80 is activated by interval timer 40 to produce a user detectable indication that an iontophoretic dose is being delivered.

The third mode of operation, the auto stimulation/dose mode, may also be accomplished through proper positioning of mode selector switch 70. In this mode, electrical tissue stimulation and iontophoretic stimulation are alternately provided under control of stimulation interval timer 20, control circuit 90 and interval timer 40. Timer 20 provides a periodic output to mode control circuit 90. In the preferred embodiment, there are several periods which may be slected including quarter hour, one-half, one hour, two hour or four hour intervals. In the one-half hour interval operation for example, timer 20 activates control circuit 90 at one-half hour intervals. After activation of circuit 90 an iontophoretic dose is delivered in the same manner as described with regard to the manual dose mode. Before and between intervals of iontophoretic dose delivery, rate oscillator 10, intensity controller 30 and output circuit 50 are enabled for producing biphasic stimulation. Thus, it will be seen that both the intervals between iontophoretic doses and the duration of the dose interval itself may be adjustable according to the needs of the patient. It will be understood that the embodiment of FIG. 1 is merely exemplary, and that the addition of further user actuated controls for adjustment of stimulation parameters is contemplated.

Figure 2:
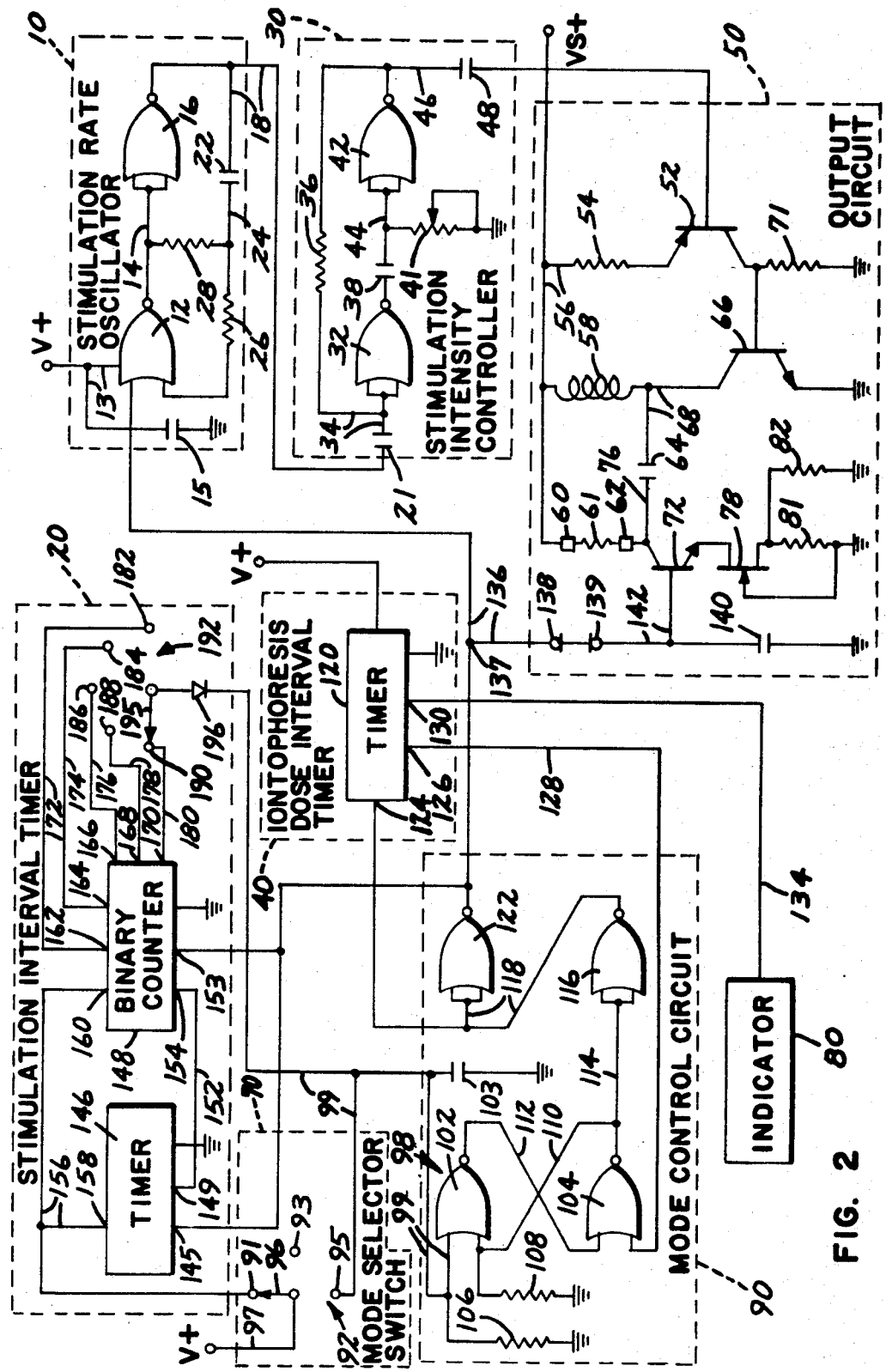
FIG. 2 is a detailed schematic diagram of the preferred embodiment of the present invention.

Referring to FIG. 2 there is illustrated the preferred embodiment of the present invention in detailed schematic diagram form. To aid the understanding of the circuit of FIG. 2, sections of the circuitry in the drawing that correspond to the functional blocks of FIG. 1 are enclosed by dashed lines. For the sake of clarity, certain power supply connections have been omitted from the diagram. Reference number 10 indicates generally a rate oscillator circuit. In the circuit, NOR-gate 12 is connected through one branch of conductor 14 to the inputs of NOR-gate 16, the output of gate 16 connected through one branch of conductor 18 to capacitor 21 and through another branch of said conductor to capacitor 22. It will be understood that NOR-gate 16, and several other NOR-gates, function as inverters, but for convenience of identification will be referred to as NOR-gates. Capacitor 22 is further connected to one end of each of resistors 26 and 28 through conductor 24. The other ends of resistors 26 and 28 are connected to the lower input of NOR-gate 12 and to conductor 14 respectively. NOR-gate 12 is connected through one branch of conductor 13 to V+ through another branch to capacitor 15, which is connected on its other side to signal ground.

Reference number 30 generally indicates the stimulation pulse intensity-control circuit. The circuit is connected to the output of rate oscillator 10 through capacitor 21 and conductor 34. Conductor 34 connects to the inputs of NOR-gate 32 and to one end of resistor 36. The output of NOR-gate 32 connects through capacitor 38 to conductor 44. Conductor 44 connects to potentiometer 41, which is connected to signal ground on its other end, and the inputs of NOR-gate 42. The output of NOR-gate 42 connects through one branch of conductor 46 to the other end of resistor 36, and through the other branch of said conductor to one side of capacitor 48.

The stimulation output circuit is generally indicated by reference number 50. It is connected to circuit 30 through capacitor 48 and the base of transistor 52. The emitter of transistor 52 is connected through resistor 54 to a positive potential VS+ and to conductor 56. VS+ may be a different voltage than V+, as required by the current and voltage requirements of output circuit 50. Conductor 56 further connects to inductor 58 and electrode 60. The other end of inductor 58 is connected to capacitor 64 and the collector of transistor 66 through conductor 68. The base of transistor 66 is connected to the collector of transistor 52 and through resistor 71 to signal ground, which also connects to the emitter of transistor 66. The collector of transistor 72 is connected to electrode 62 and to capacitor 64 through conductor 76. FET 78 connects through its drain to the emitter of transistor 72. The source of FET 78 is connected through parallel resistors 81 and 82 to signal ground, which also connects to the gate of FET 78.

Reference number 90 generally indicates the mode control circuit. Flip-flop circuit 98 comprises NOR-gates 102 and 104. The upper input of NOR-gate 102 is connected to contact 95 of three position switch 92 through one branch of conductor 99, and to signal ground through another branch of conductor 99 and a resistor 106. Pole 96 of switch 92 is connected to V+ through a conductor 97. The upper input of NOR-gate 102 also connects to capacitor 103, which is connected on its other side to signal ground. The lower input to NOR-gate 102 is connected through a resistor 108 to signal ground and to the output of NOR-gate 104 through conductor 110. The output of NOR-gate 102 is connected to the upper input of NOR-gate 104 through conductor 112. The output of NOR-gate 104 is connected through a conductor 114 to both inputs of NOR-gate 116, the output of which is connected through one branch of conductor 118 to an input 124 of dose interval timer 120 and through the other branch of said conductor to both inputs of NOR-gate of 122. An output 126 of timer 120 connects to the lower input of NOR-gate 104 through conductor 128. Output 130 of one shot timer 120 is connected to an indicator 80 through conductor 134. The output of NOR-gate 122 is connected through one branch of conductor 136 to the upper input of NOR-gate 12, through another branch to the anode of diode 138, to input 145 of timer 146 and input 153 of binary counter 148. The cathode of diode 138 connects to the cathode of diode 139. The anode of diode 139 connects to the base of transistor 72 through a conductor 142, and through a capacitor 140 to signal ground.

Reference numeral 20 generally indicates the stimulation interval timer circuit including timer 146 and binary counter 148. Output 149 of timer 146 connects through conductor 152 to input 154 of binary counter 148. A conductor 156 connects from contact 91 of switch 92 the respective power supply inputs 158 and 160 of timer 146 and binary counter 148 through the respective branches of conductor 156. Outputs 162, 164, 166, 168 and 170 of binary counter 148 connect through conductors 172, 174, 176, 178 and 180 to contacts 182, 184, 186, 188 and 190 of five position switch 192 respectively. Pole 195 of switch 192 connects through a diode 196 to one branch of conductor 99. It will be understood that a device on-off switch and a power source are provided as is well known in the art, but have been omitted from the drawing for the purpose of clarity.

The operation of the preferred embodiment of the present invention will now be explained with reference to FIG. 2. Stimulation only mode is selected by setting pole 96 of switch 92 to contact 93. In this mode, oscillator 10 is free to oscillate at a frequency defined by cooperation of resistor 28 and capacitor 22. The resultant output wave on conductor 18 periodically triggers circuit 30 through capacitor 21 in order to produce output pulses on conductor 46 the width of which are adjustable through potentiometer 41. The pulses appearing on conductor 46 are passed through capacitor 48, periodically triggering transistor 52 and in turn transistor 66. The triggering of transistor 66 causes a momentary voltage potential to develop across inductor 58 and thereby cause, in cooperation with capacitor 46, biphasic stimulation pulses across tissue load 61 as are generally known in the art. For example, see biphasic waveforms 250 and 252 shown in FIG. 3. The preferred embodiment of the present invention produces biphasic waveform 250, but may be adapted to produce waveform 252 or any other generally known in the art.

In the manual dose mode, the initiation of the iontophoretic dose is accomplished manually by momentary connection of switch 92's pole 96 to contact 95. Preferably, the pole is spring biased to return it automatically to contact with contact 93. Said momentary connection applies a positive potential V+ at the upper input to NOR-gate 102. Immediately thereafter, the output of NOR-gate 116 transitions from a logic high to a logic low level and thereby triggers dose interval timer 120 by way of input 124. In response thereto, timer 120 begins timing an iontophoresis dose interval after which it produces a high level signal at its output 126 and consequently the input of NOR-gate 104. It will be seen that timer 120 may be of digital or analog design and may be externally adjustable to provide selectable intervals of iontophoretic stimulation. Throughout the iontophoretic stimulation interval, oscillator 10 is inhibited via a high level signal produced on conductor 136 and present at the upper input NOR-gate 12. The delivery of biphasic stimulation pulses is thereby suspended. The high level signal present on conductor 136 also actuates transistor 72 through conductor 142 and constant current diodes 138 and 139. Diodes 138 and 139 cooperate with capacitor 140 to provide gradual activation and deactivation of transistor 72, thereby avoiding tetanizing of the patient's muscle tissue. With transistor 72 in its "on" condition, a constant DC current flows from conductor 56 through electrode 60, tissue 61, electrode 62, transistor 72 and constant current FET 78 to signal ground via resistors 80 and 82. The level of DC current delivered is adjustable or presettable via resistor 82, which may be a potentiometer.

During an iontophoretic stimulation interval, timer 120 activates indicator 80 via output 130 and conductor 134. Indicator 80 serves to provide a visual signal to the user throughout the interval indicating the delivery of iontophoretic stimulation and may also serve to indicate device battery strength if desired.

At the end of the iontophoretic dose interval, output 126 of timer 120 resets flip-flop 98 via conductor 128 and the lower input of NOR-gate 104. Upon reset, oscillator 10 is enabled via the output of NOR-gate 122 to conductor 136, while transistor 72 is deactivated via diodes 138, 139 and conductor 142. Biphasic electrical tissue stimulation is thereby resumed.

Generally, any electrodes capable of use with an iontophoretic drug delivery system will suffice for electrodes 60 and 62. When the present invention is producing iontophoretic stimulation the electrodes operate in the same manner as when used with a dedicated iontophoretic device. The ionic substance contained within one of the electrodes or both is driven via the iontophoretic DC current through the skin and into the body tissue. However, when the present invention is producing biphasic stimulation the electrodes and the ionic substance or substances contained therein must act principally as a conduit for that delivery of the biphasic current to the underlying tissue; so given a biphasic current, there is no significant movement of the ionic substance into the body tissue. This criteria must be met for the electrodes to be suitable for use with the present invention. In this manner, the same electrodes which provide for the delivery of iontophoretic substances may also be utilized for delivering biphasic stimulation.

Positioning switch 92's pole 96 on contact 91 causes the present invention to be in the auto stimulation/dose mode. In this mode biphasic electrical tissue stimulation and iontophoretic stimulation are alternately provided under control of stimulation interval timer 20. Upon application of power, via switch 92, to timer 146 and binary counter 148 at the respective power supply inputs 158 and 160, timer 146 produces a periodic output signal at output 149. This signal is carried over conductor 152 to the clock input 154 of binary counter 148. Outputs 162, 164, 166, 168 and 170 of binary counter 148 comprise selected output bits of the counter 148 binary outputs. Several less significant bit outputs Q0 through Q9 are left unconnected and for that reason are not shown in the drawing. Output 170 (Q10) of counter 148 has a period of 15 minutes given a suitable clock signal from timer 146. Similarly, outputs 168, 166, 164 and 162 have periods of ½ hours 1 hours, 2 hours and 4 hours respectively. Pole 195 of switch 192 may be selectively positioned to any of the switch contacts 182, 184, 186 188 or 190 so that any of the periodic signals produced by counter 148 may be connected to conductor 99. Diode 196 serves to isolate binary counter 148's outputs when a V+ signal is applied through switch 92 and contact 95 for a manual dose.

The occurrence of a high signal on conductor 99 sets flip-flop 98 and initiates a dose interval like previously described with respect to manual dose operation. At the end of the dose interval the stimulation output reverts back to biphasic electrical tissue stimulation until the occurrence of the next low to high signal transition from counter 148 on conductor 99. It will be seen that the intervals between iontophoretic doses may be controlled using switch 192 to control the period at which said low to high transition occurs on conductor 99 by selecting the desired counter 148 output.

With the modification to conductor 136 illustrated in FIG. 4 the present invention may provide iontophoretic and biphasic stimulation simultaneously, in which case the output waveform appears as illustrated for the time interval $t_0$ to $t_1$ in FIG. 5. The circuit shown in FIG. 4 is identical to that of FIG. 2 with the exception of the modification; however, portions of the circuit have been omitted from FIG. 4 for the sake of brevity. As shown, the biphasic waveform is superimposed on the dc voltage required to deliver the predetermined iontophoretic current. Therefore the dc voltage bias point of the biphasic waveform may vary as tissue impedance changes. As illustrated in FIG. 4, the preferred embodiment of the present invention may be modified to produce the simultaneous iontophoretic and biphasic stimulation waveform illustrated in FIG. 5 by breaking conductor 136 between node 137 and the input of the stimulation rate oscillator 10 and tying the input to the rate oscillator 10 to signal ground. Conductors 136a and 136b represent conductor 136 after such modification. So modified, the present invention continuously produces biphasic electrical tissue stimulation whenever activated i.e. turned on, and selectively provides that biphasic stimulation superimposed on an iontophoretic current in response to appropriate positioning mode selector switch 70. Switch 70 functions to control stimulation mode in the same manner as was described with reference to the preferred embodiment of FIG. 2 except that the iontophoretic current produced during an iontophoresis dose interval includes the superimposed biphasic stimulation. In FIG. 5, the DC bias voltage transition at time $t_1$ illustrates the automatic cessation of the iontophoretic component of the stimulation waveform at the end of a timed iontophoretic dose, which leaves only the non-polorized biphasic waveform until another iontophoretic dose is initiated, which may be automatically as in the auto stimulation/dose mode or manually as in the manual dose mode.

It will be understood that there may be added to the embodiment of FIG. 2 further user actuated controls for adjustment of stimulation parameters such as frequency and intensity. It will also be seen that the present invention, as embodied in FIG. 2, makes it practical to utilize the electrotherapeutic method of alternating or interchanging iontophoretic stimulation and biphasic electrical tissue stimulation. Still further, it will be seen that in the automatic mode the present invention has the capability to accurately schedule iontophoretic drug dosage without resort to user intervention. A still further advantage is the automatic initiation of scheduled dosages while permitting, if desireable, manually actuated dosages. Still further, it will be seen that the present invention may easily be modified to prevent unwanted user intervention by providing a user control lockout, as in the case of children or the mentally incapacitated.

It will be understood that various circuit designs are capable of producing the result achieved by the present invention. Therefore, the illustrations and descriptions set forth in this application are merely illustrative of the present preferred embodiment of the invention and are in no way meant as a limitation on circuit configuration. It is contemplated that the inventive concept as illustrated herein may be achieved by means of microprocessor control or any combination of analog and/or digital technologies. It is also contemplated that more elaborate timing circuits could be utilized to provide sophisticated stimulation schedules.

What is claimed is:

1. An electrotherapeutic device for use with electrodes adaptable for introducing iontophoretic substances and delivering electrical tissue stimulation to body tissue, comprising:
    generating means operative in a first mode for producing electrical tissue stimulation and operative in a second mode for producing iontophoretic current;
    a pair of output terminals for connection to electrodes, said output terminals connected to said generating means; and
    means for controlling the mode of operation of said generating means for causing either iontophoretic current or electrical tissue stimulation to be delivered to the terminals for application to body tissue.

2. A device according to claim 1 wherein said control means includes timing means having a user actuated switch for causing said generating means to operate in said second mode for a predetermined interval, and means for causing sid generating means to operate in said first mode between intervals of operation in said second mode.

3. A device according to claim 1 wherein said control means includes timing means for causing said generating means to automatically alternate between said modes operation, each of said modes lasting a predetermined interval.

4. A device according to claim 1 including indicating means connected to said control means for providing a user detectable signal indicative of which mode said generating means is operating in.

5. An electrotherapeutic device for use with electrodes adaptable for introducing iontophoretic substances and delivering electrical tissue stimulation to body tissue, comprising:
   electrical tissue stimulation generating means;
   iontophoretic current generating means;
   means for connecting said generating means to common output terminals; and
   control means connected to both of said generating means for actuating either of said generating means whereby iontophoretic current or electrical tissue stimulation may be selectively delivered to said terminals for application to body tissue.

6. A device according to claim 5 wherein said control means includes a user controlled timing means for actuating said iontophoretic generating means for a predetermined time interval, and means for actuating said electrical tissue stimulation generating means at the end of said timed interval whereby manually initiated timed intervals of iontophoretic current may be delivered to body tissue, after which the delivery of electrical tissue stimulation is automatically reinitiated.

7. A device according to claim 5 wherein said control means includes timing means for actuating said iontophoretic current generating means for a first predetermined time interval and for actuating said electrical tissue stimulation generating means for a second predetermined time interval beginning at the end of said first interval, said control means further including means for reactuating said iontophoretic current generating means at the end of said second interval whereby intervals of iontophoretic current interspersed with intervals of electrical tissue stimulation are delivered to said output terminals.

8. A device according to claim 5 including indicating means connected to said control means for providing a user detectable signal indicating which generating means is actuated.

9. A device according to claim 1 or 5 wherein said means for generating electrical tissue stimulation produces biphasic current.

10. An electrotherapeutic device for use with electrodes adaptable for introducing iontophoretic substances and delivering electrical tissue stimulation body to tissue, comprising:
   generating means having means operative in a first mode for producing electrical tissue stimulation and means operative in a second mode for producing iontophoretic current;
   a pair of output terminals for connection to electrodes, said output terminals receiving the output of said generating means; and
   control means for causing said generating means to normally operate in said first mode and for causing said generating means to operate in said second mode for a predetermined time interval and then automatically revert to said first mode of operation.

11. A device according to claim 10 wherein said control means includes timing means for causing said generating means to automatically alternate between said operative modes, each mode lasting for a predetermined time interval.

12. An electrotherapeutic device for use with electrodes adaptable for introducing iontophoretic substances and delivering electrical tissue stimulation body to tissue, comprising:
   generating means having means operative in a first mode for producing electrical tissue stimulation and means operative in a second mode for producing iontophoretic current;
   a pair of output terminals for connection to electrodes, said output terminals receiving the output of said generating means; and
   control means having first means for causing said generating means to normally operate in said first mode and for selectively causing said generating means to operate in said second mode for a predetermined time interval and then automatically revert to said first mode of operation, and having second means for causing said generating means to automatically alternate between said modes of operating, each of said modes lasting an independently controlled predetermined time interval.

13. An electrotherpeutic device for use with electrodes adaptable for introducing iontophoretic substances and delivering electrical tissue stimulation to body tissue, comprising:
   generating means having means operative in a first mode for producing electrical tissue stimulation and having means operative in a second mode for producing electrical tissue stimulation superimposed on an iontophoretic current;
   a pair of output terminals for connection to electrodes, said output terminals receiving the output of said generating means; and
   means for controlling the mode of operation of said generating means.

14. An electrotherapeutic device for use with electrodes adaptable for introducing iontophoretic substances and delivering electrical tissue stimulation to body tissue, comprising:
   generating means operative in a first mode for producing electrical tissue stimulation and operative in a second mode for producing electrical tissue stimulation superimposed on an iontophoretic current;
   a pair of output terminals for connection to electrodes, said output terminals connected to said generating means; and
   means for controlling the mode of operation of said generating means for causing either electrical tissue stimulation superimposed on an iontophoretic current or nonpolarized electrical tissue stimulation to be delivered to the terminals for application to body tissue.

15. A device according to claim 13 or 14 wherein said control means includes timing means having a user actuated switch for causing said generating means to operate in said second mode for a predetermined time interval and means for causing said generating means to operate in said second mode between intervals of operation in said first mode.

16. A device according to claim 13 or 14 wherein said control means includes timing means for causing said generating means to automatically alternate between said modes operation, each of said modes lasting a predetermined time interval.

17. A device according to claim 13 or 14 including indicating means connected to said control means for providing a user detectable signal indicative of which mode said generating means is operating in.

18. An electrotherapeutic device for use with electrodes adaptable for introducing iontophoretic substances and delivering electrical tissue stimulation to body tissue, comprising:

electrical tissue stimulation generating means;

iontophoretic current generating means;

means for connecting said generating means to common output terminals; and control means operatively connected for actuating said generating means either individually or simultaneously whereby iontophoretic current or electrical tissue stimulation or electrical tissue stimulation superimposed on an iontophoretic current may be selectively delivered to said terminals for application to body tissue.

19. A device according to claim 18 wherein said control means includes a user controlled timing means for selectively actuating said iontophoretic generating means or said electrical tissue stimulation generating means for predetermined time intervals.

20. An electrotherapeutic device for use with electrodes adaptable for introducing ionic substances and electrical tissue stimulation to body tissue, comprising:

presettable timing means for producing alternating first and second timing signals having predetermined durations;

oscillator means actuated by said first timing signal for producing periodic pulses of adjustable frequency;

modulation means connected to said oscillator means for modulating the duty cycle of said pulses;

biphasic current generating means actuated by said first timing signal and connected to receive said modulated pulses for producing biphasic current at a frequency and intensity respectively proportional to the frequency and duty cycle of said pulses;

iontophoretic current generating means actuated by said second timing signal for producing iontophoretic current at an adjustable level; and output means connected to said biphasic current generating means and said iontophoretic current generating means for alternately delivering biphasic or iontophoretic current to said electrodes according to said timing signals.

21. A device according to claim 20 wherein said timing means includes a user actuated switch and a oneshot timer responsive to said switch for causing iontophoretic current to be channeled to said electrodes for a predetermined interval, and means for deactivating said oscillator means during said interval.

* * * * *